(12) United States Patent
Hardert et al.

(10) Patent No.: US 8,167,903 B2
(45) Date of Patent: May 1, 2012

(54) DEVICE FOR RETRIEVING A FOREIGN OBJECT LOCATED IN A BODY VESSEL

(75) Inventors: Michael W. Hardert, Bloomington, IN (US); Michael D. Deckard, Solsberry, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 309 days.

(21) Appl. No.: 12/132,836

(22) Filed: Jun. 4, 2008

(65) Prior Publication Data

US 2009/0306678 A1 Dec. 10, 2009

(51) Int. Cl.
*A61M 29/00* (2006.01)
(52) U.S. Cl. .............. 606/200; 606/127; 606/198
(58) Field of Classification Search ............ 606/127, 606/200, 208, 113, 114, 198, 110; 623/1.22, 623/1.11, 1.49; 604/96.01
See application file for complete search history.

(56) References Cited

U.S. PATENT DOCUMENTS

| | | | |
|---|---|---|---|
| 4,580,568 A | 4/1986 | Gianturco | |
| 4,873,978 A * | 10/1989 | Ginsburg | 606/198 |
| 6,511,497 B1 * | 1/2003 | Braun et al. | 606/200 |
| 6,805,707 B1 | 10/2004 | Hong et al. | |
| 6,827,733 B2 | 12/2004 | Boneau | |
| 6,945,977 B2 | 9/2005 | Demarais et al. | |
| 7,108,707 B2 | 9/2006 | Huter et al. | |
| 7,153,322 B2 | 12/2006 | Alt | |
| 7,179,289 B2 | 2/2007 | Shanley | |
| 2003/0045897 A1 | 3/2003 | Huter et al. | |
| 2003/0212430 A1 * | 11/2003 | Bose et al. | 606/200 |
| 2005/0038468 A1 * | 2/2005 | Panetta et al. | 606/200 |
| 2005/0165442 A1 * | 7/2005 | Thinnes et al. | 606/200 |
| 2007/0016243 A1 | 1/2007 | Ramaiah et al. | |
| 2008/0269774 A1 * | 10/2008 | Garcia et al. | 606/127 |

* cited by examiner

*Primary Examiner* — Ryan Severson
*Assistant Examiner* — Tin Nguyen
(74) *Attorney, Agent, or Firm* — Brinks Hofer Gilson & Lione

(57) ABSTRACT

In at least one embodiment of the present invention, a retrieval device for entrapping and retaining a foreign object located in a body vessel for its extraction therefrom is provided. The device comprises a cage having a proximal end and a distal end and a longitudinal axis extending between the proximal and distal ends. The cage is radially expandable about the longitudinal axis to define an expanded state and to form an opening at the distal end for receiving the foreign object. The cage is collapsible to define a collapsed state and to retain the foreign object therein such that the foreign object is substantially aligned with the longitudinal axis. Extending proximally from the proximal end of the cage is a cable for retrieval of the device in the collapsed state.

20 Claims, 5 Drawing Sheets

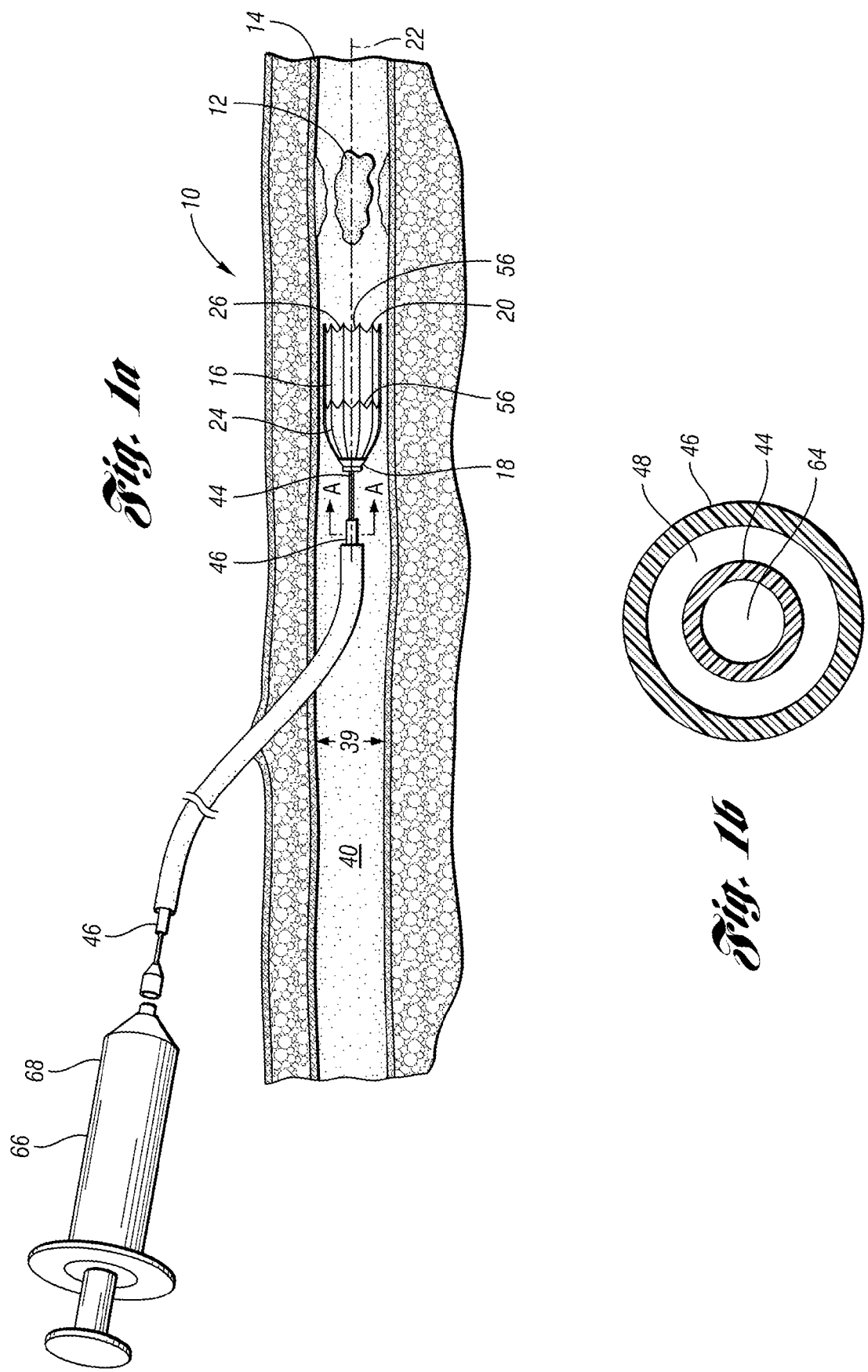

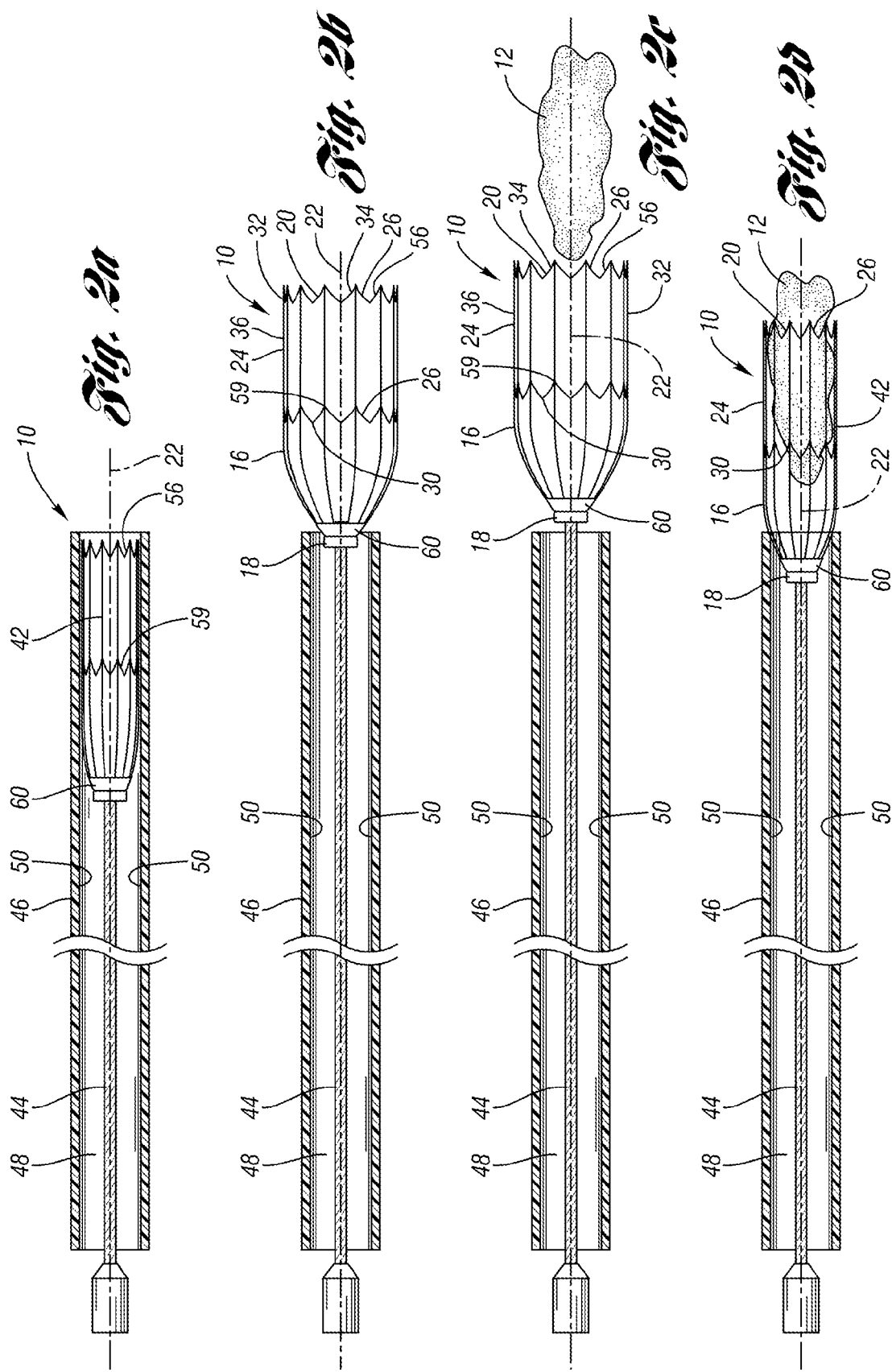

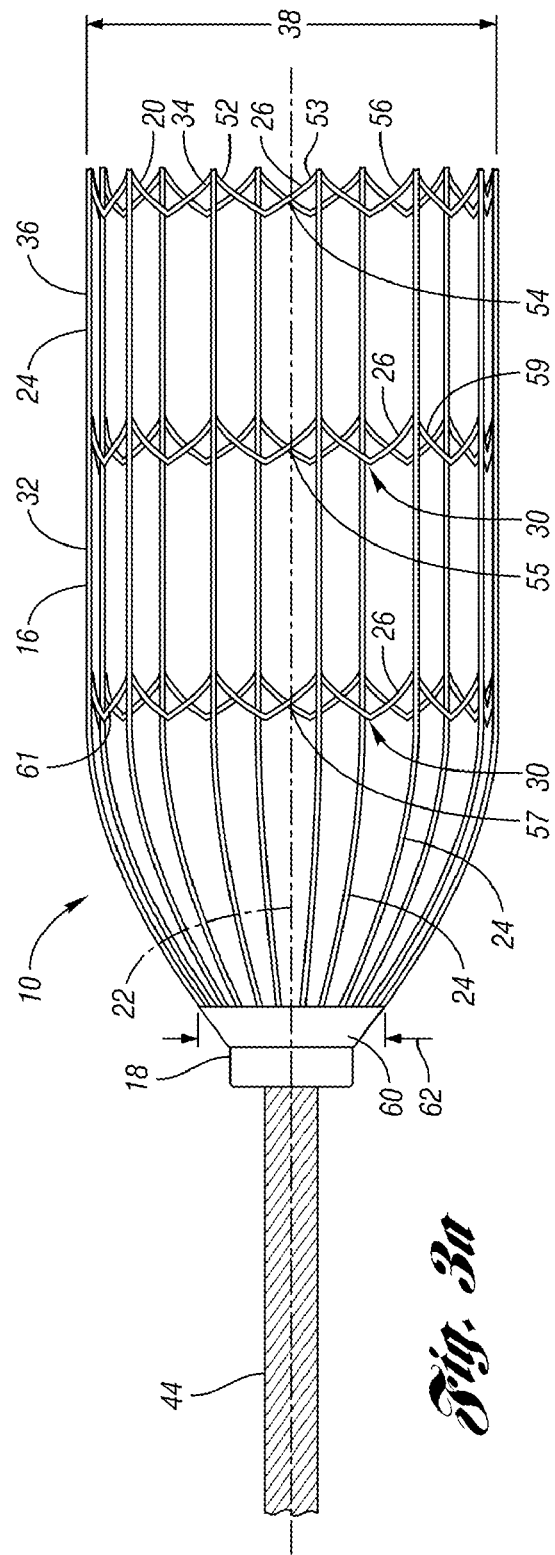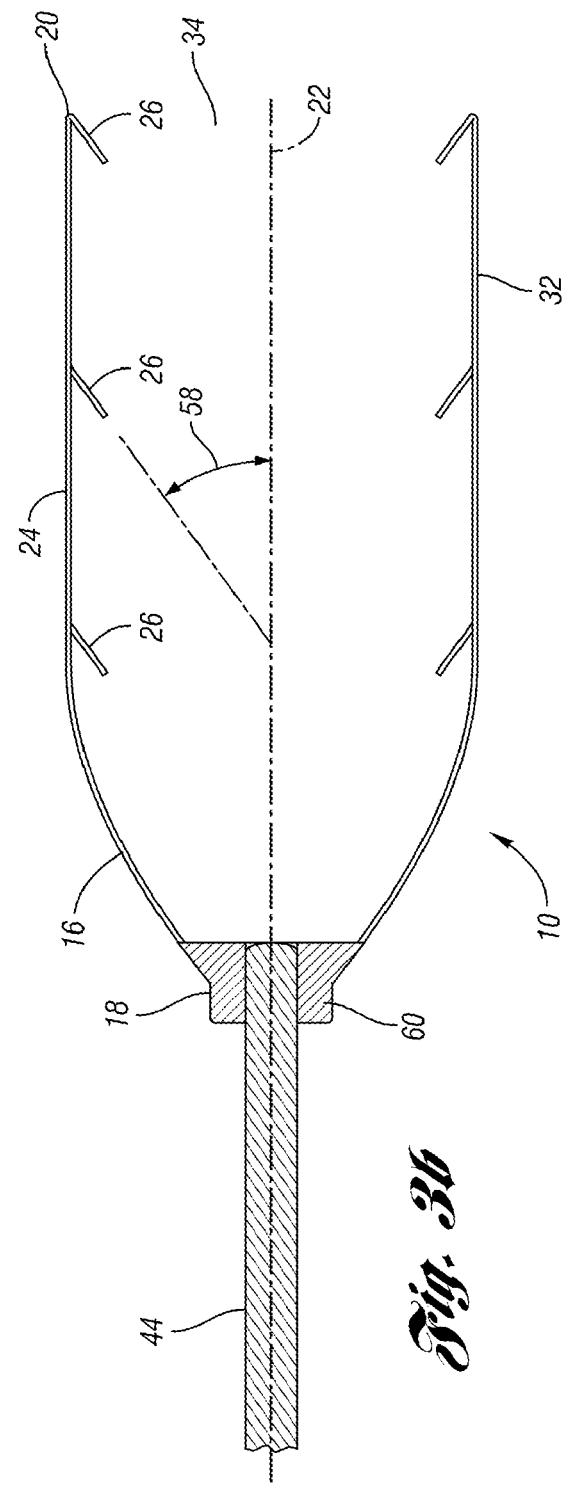
Fig. 3a
Fig. 3b

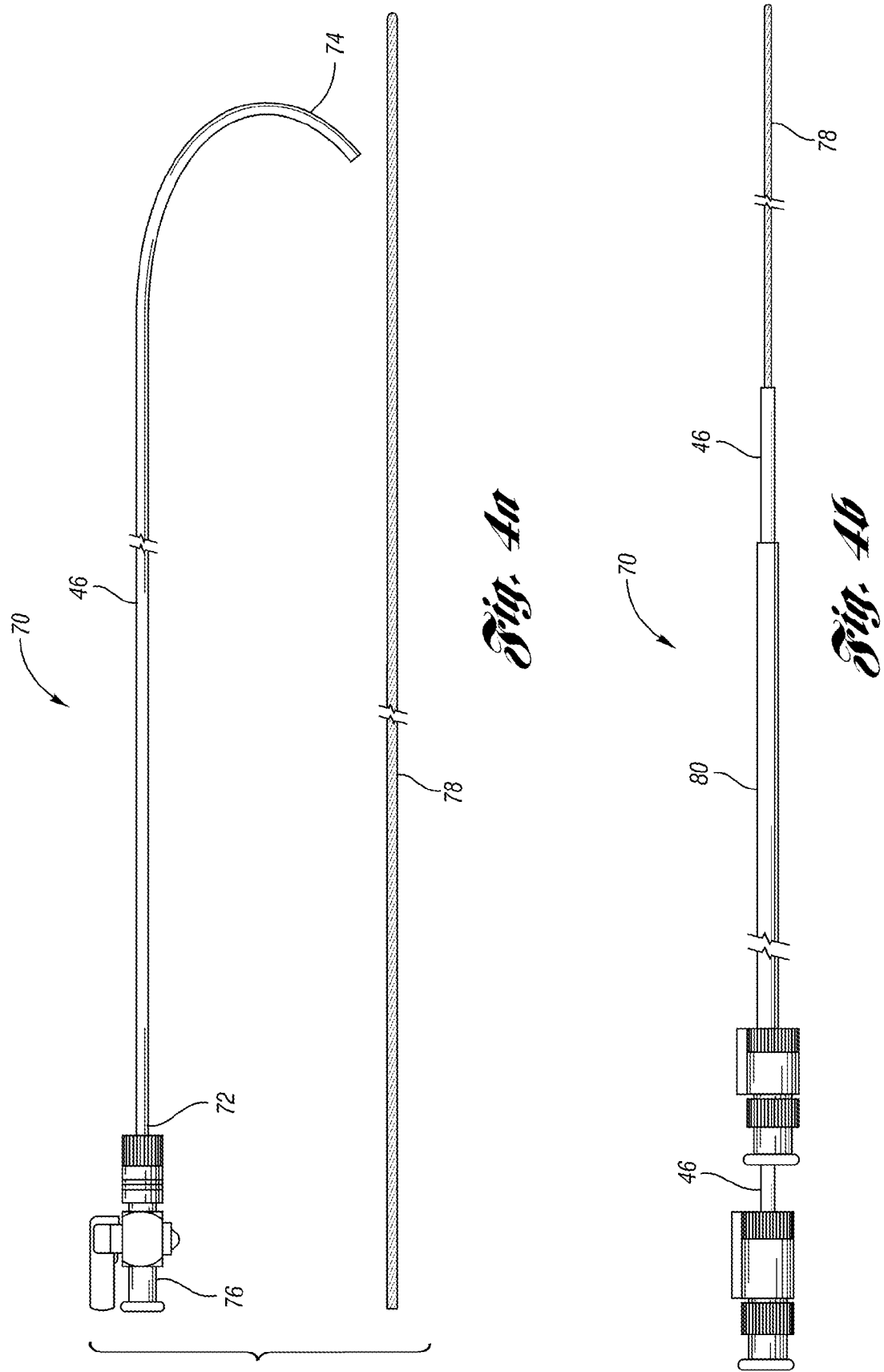

DEVICE FOR RETRIEVING A FOREIGN OBJECT LOCATED IN A BODY VESSEL

BACKGROUND OF THE INVENTION

1. Field of the Invention

The present invention relates to an extraction device capable of capturing and retrieving objects from hollow bodies, and in particular, to a medical instrument for entrapping and removing an object from a body.

2. Background

Various instruments are known in the art for removing foreign objects from the body. For example, such instruments are used for removal of stones such as kidney stones, gall stones, and the like from various sites along the urinary tract of the patient's body. Retrieval devices are also widely used for removing foreign articles from the vascular system of a patient. In such a case, examples of the foreign articles include vena cava filters and parts of medical devices such as catheters, guide wires, cardiac leads, etc., which may break and become detached during medical procedures.

Some of these instruments employ a snare configured as a single distal loop which is positioned over a free end of the foreign body, and which is collapsed and tightened around the foreign body. One drawback to such a retrieval device is that the foreign object may be difficult to hook with the distal loop of the snare, which may require significant manipulation in order to capture the foreign object. Another drawback is that although the distal hook may capture the foreign object, retrieval of the foreign object may be difficult. This is because during retrieval of the foreign object the hook and the captured object are typically misaligned with the axis of the sheath, thereby hindering retraction of the hook and the foreign object into the sheath.

BRIEF SUMMARY OF THE INVENTION

This invention is related to an extraction device for entrapping and removing an object from a body which may address the concerns discussed in the foregoing paragraphs.

In at least one embodiment of the present invention, a retrieval device for entrapping and retaining a foreign object located in a body vessel for its extraction therefrom is provided. The device comprises a cage having a proximal end and a distal end and a longitudinal axis extending between the proximal and distal ends. The cage is radially expandable about the longitudinal axis to define an expanded state and to form an opening at the distal end for receiving the foreign object. The cage is collapsible to define a collapsed state and to retain the foreign object therein such that the foreign object is substantially aligned with the longitudinal axis. Extending proximally from the proximal end of the cage is a cable for retrieval of the device in the collapsed state.

In one aspect, the cage includes a plurality of longitudinal bars extending between the proximal and distal ends of the cage. A plurality of struts connect the longitudinal bars together. Each strut has a pivotal joint which together fold to collapse the longitudinal bars along the longitudinal axis to define the collapsed state of the cage. The pivotal joints unfold to move the longitudinal bars radially outward from the longitudinal axis to define the expanded state of the cage.

In at least one other embodiment of the present invention, a retrieval kit for entrapping and retaining a foreign object located in a body vessel for its extraction therefrom is provided. The kit comprises a retrieval device as recited in the foregoing paragraph. A sheath is included for positioning in the body vessel. The cage is configured to be disposed within the sheath in the collapsed state and to be advanced out of the sheath for expanding into the expanded state. The cage is recovered via the cable into the sheath to retrieve the device in the collapsed state.

In at least another embodiment of the present invention, a method for entrapping and retaining a foreign object located in a body vessel for its extraction therefrom is provided. The method comprises deploying a retrieval device within the body vessel. The device includes a cage having a proximal end and a distal end and a longitudinal axis extending between the proximal and distal ends. The cage is radially expanded about the longitudinal axis to form an opening at the distal end that receives the foreign object. The cage is collapsed via a cable extending proximally from the proximal end of the cage for retrieval of the device. The foreign object is retained in the cage such that the foreign object is substantially aligned with the longitudinal axis.

Further objects, features, and advantages of the invention will become apparent from consideration of the following description and the appended claims when taken in connection with the accompanying drawings.

BRIEF DESCRIPTION OF THE DRAWINGS

FIG. 1a is an environmental view of a retrieval device in accordance with an embodiment of the present invention;

FIG. 1b is a cross-sectional view of the retrieval device depicted in FIG. 1a;

FIG. 2a is a side view of the retrieval device within a sheath in the collapsed state;

FIG. 2b is a side view of the retrieval device in the expanded state;

FIG. 2c is a side view of the retrieval device in the expanded state receiving a foreign object;

FIG. 2d is a side view of the retrieval device being retrieved in the collapsed state;

FIG. 3a is a side view of a retrieval device in accordance with an embodiment of the present invention;

FIG. 3b is a cross-sectional view of the retrieval device depicted in FIG. 3a;

FIG. 4a is an exploded view of a retrieval kit in accordance with an embodiment of the present invention;

FIG. 4b is a side view of a retrieval kit in accordance with another embodiment of the present invention.

DETAILED DESCRIPTION OF THE INVENTION

Figure 5:
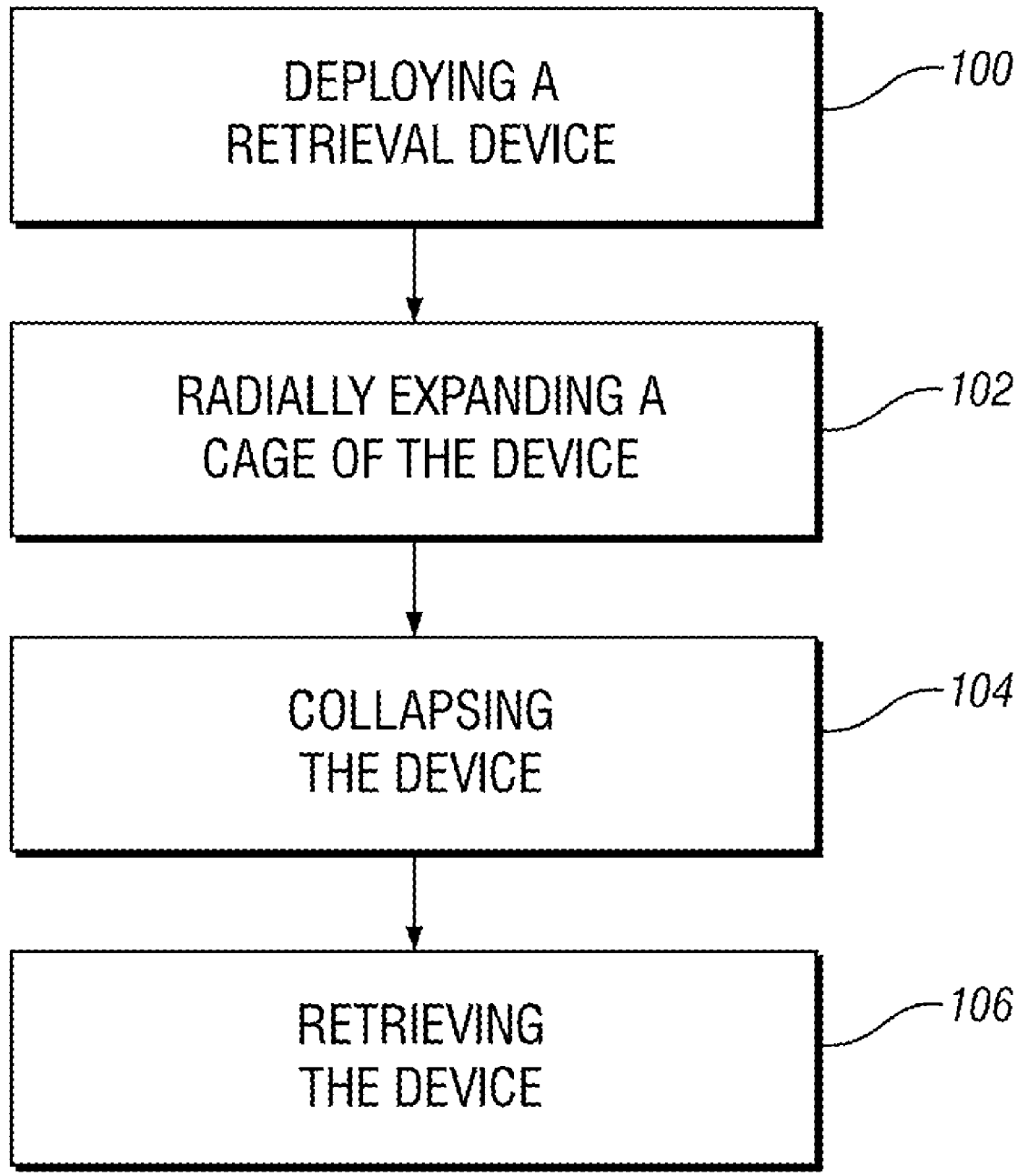
FIG. 5 is a flow chart for a method for entrapping and retaining a foreign object located in a body vessel in accordance with an embodiment of the present invention.

Detailed embodiments of the present invention are disclosed herein. It is understood however, that the disclosed embodiments are merely exemplary of the invention and may be embodied in various and alternative forms. The figures are not necessarily to scale; some figures may be configured to show details of a particular component. Therefore, specific structural and functional details disclosed herein are not to be interpreted as limiting but merely as a representative basis with the claims and for teaching one skilled in the art to practice the present invention.

Embodiments of the present invention provide a retrieval device that includes a cage. The cage is radially expandable about a longitudinal axis to form an opening at the distal end. The open distal end receives a foreign object located in a body vessel. In one example, the cage is moved distally in the body vessel such that the open distal end advances around the foreign object, thereby reducing the amount of manipulation necessary to entrap the foreign object. Preferably, the foreign object is aligned with the longitudinal axis and the cage is collapsed to retain the foreign object therein. In another example, the collapsed cage containing the longitudinally aligned foreign object has reduced interference with a sheath that is used for recovering the device, thereby facilitating retrieval of the foreign object from the body vessel.

Now referring to FIGS. 1a-3b, a retrieval device 10 is provided for capturing and removing a foreign object 12 located in a body vessel 14. The device 10 includes a cage 16 that has a proximal end 18 and a distal end 20. A longitudinal axis 22 extends between the proximal and distal ends 18 and 20. The cage 16 is formed from a plurality of longitudinal bars 24 that extend between the proximal and distal ends 18 and 20. The longitudinal bars 24 are connected together by a plurality of struts 26. Each of the struts 26 have a pivotal joint 30 preferably formed near the center of the strut 26. As illustrated in FIGS. 1a, 2b-2c and 3a, the pivotal joints 30 may be unfolded to move the longitudinal bars 24 radially outward from the longitudinal axis 22 to define an expanded state 32 of the cage 16. In the expanded state 32, the cage 16 has an opening 34 formed at the distal end 20. The opening 34 of the cage 16 is for capturing the foreign object 12.

In one embodiment, the cage 16 forms a cylindrical portion 36 in the expanded state 32. The cylindrical portion 36 preferably entraps the foreign object 12 such that the foreign object 12 is substantially aligned with the longitudinal axis 22. Moreover, the shape of the cylindrical portion 36 may at least vaguely correspond to the shape of certain foreign objects 12 which may facilitate capturing and retaining the foreign object 12 within the cage 16. For example, the foreign object 12 may have a substantially cylindrical shape, e.g., the tip of catheter, which may be neatly nested within the cage 16 subsequent to the cage 12 being advanced over the cylindrical object 12.

In another embodiment, the cage 16 in the expanded state 32 has a maximum diameter 38 less than a diameter 39 of the lumen 40 of the body vessel 14. This allows the expanded cage 16 to be moved both distally and proximally within the body vessel 14 with minimal effort, preferably making capturing and retrieval of the foreign object 12 easier, as will be discussed in greater detail below.

The pivotal joints 30 may be folded to collapse the longitudinal bars 24 along the longitudinal axis 22, thereby collapsing the cage 16 and defining a collapsed state 42. As illustrated in FIG. 2d, the cage 16 collapses to retain the foreign object 12 within the cage 16. In one example, the longitudinal bars 24 move radially inward toward the longitudinal axis 22 to position and align the foreign object 12 with the longitudinal axis 22. The longitudinal bars 24 also retain or hold the foreign object 12 substantially aligned with the longitudinal axis 22 during retrieval of the foreign object 12 from the body vessel 14.

The device 10 further includes a cable 44 extending proximally from the proximal end 18 of the cage 16. The cable 44 is used to retrieve the device 10 in the collapsed state 42. In one example, the cable 44 is pulled proximally through the vessel 14 to move the cage 16 into a lumen 48 of a sheath 46. In another example, the cable 44 is used to hold the cage 16 steady or stationary in the vessel 14 while the sheath 46 is advanced over the cage 16. In either scenario, walls 50 of the sheath 46 press against the radially expanded longitudinal bars 24 and the struts 26, generating force to fold the struts 26, thereby causing the cage 16 to collapse. Preferably, the collapsed cage 16 and the sheath 46 are retracted together from the vessel 14 to retrieve the foreign object 12. Moreover, the cage 16 containing the longitudinally aligned foreign object 12 may be more aligned with the lumen 48 of the sheath 46 so as to reduce interference with the sheath 46, facilitating advancement of the cage 16 into the lumen 48 and retraction of the foreign object 12 from the body vessel 14.

In at least one embodiment, the cage 16 is self-expanding. The walls 50 of the sheath 46 may restrain the cage 16 in the collapsed state 42 when the cage is disposed within the sheath 46. However, when the device 10 is deployed the cage 16 is advanced out of the sheath 46, freeing the cage 16 from the restraining walls 50. The cage 16 then self-expands to the expanded state 32. In one example, the two ends 52 and 53 of each strut 26 are connected respectively to two adjacent longitudinal bars 24. When released, the self-expanding struts 26 unfold to push the ends 52 and 53 against the longitudinal bars 24 providing force to move the bars 24 radially outward to the expanded state 32.

The struts 26 may also be circumferentially aligned about a location 54 along the longitudinal axis 22 to form a ring 56 which is connected to each of the longitudinal bars 24. As illustrated in FIGS. 1a and 2a-3a, the cage 16 may have a plurality of rings 56, 59 and 61 formed by circumferentially aligning a plurality of struts 26 about a plurality of corresponding locations 54, 55 and 57 along the longitudinal axis 22. It is believed that the ring configurations 56, 59 and 61 enhance the structure, actuation and dimensional stability of the cage 16 between the expanded and collapsed states 32 and 42. Preferably, a ring 56 is formed at the distal end 20 of the cage 16 to circumferentially align the distal ends of the longitudinal bars 24 to define a more dimensionally stabile opening 34.

As illustrated in FIGS. 2d, 3a and 3b, the struts 26 may be configured to enhance retention of the foreign object 12 within the cage 16. The pivotal joints 30 may extend from their ends 52 and 53 generally towards the proximal end 18 of the cage 16. In the expanded state 32, each strut 26 may have a configuration corresponding to a "V" shape with the pivotal joint 30 formed at the base of the "V." Preferably, the struts 26 are also biased inwardly towards the longitudinal axis 22 to form an angle 58 with the longitudinal axis 22. In one example, the angle 58 is less than about 45°. In this scenario, the struts 26 may act as "shark teeth", engaging or biting into the foreign object 12 to hinder the foreign object 12 from moving distally out of the cage 16 against the inwardly biased struts 26. Moreover, when the cage 16 is collapsed the struts 26 may be further driven into the foreign object 12 to enhance retention of the foreign object 12 in the cage 16.

The cage 16 may further include a connecting joint 60. The connecting joint 60 is disposed at the proximal end 18 of the cage 16. Each of the longitudinal bars 24 are connected to the connecting joint 60 which is connected to the cable 44. Preferably, the connecting joint 60 has a diameter 62 which is less than a maximum diameter 38 of the cage 16 in the expanded state 32. In one example, the diameter 62 of the connecting joint 60 is defined by its connection with the longitudinal bars 24. In this configuration, the longitudinal bars 24 taper inwardly along a proximal direction of the longitudinal axis 22 when in the expanded state 32.

Referring to FIGS. 1a and 1b, the cable 44 may have a lumen 64 formed therethrough. The lumen 64 is for providing fluid communication between the cage 16 and an aspirating source 66 and/or an injection source 68. In one example, a syringe-plunger device may be used as either the aspirating and/or injecting source 66 and 68. The syringe may be coupled to the lumen 64 and the plunger may be retracted to aspirate the cage 16. Alternatively, the plunger may be advanced to inject material into the cage 16. For instance, the injection source 68 may inject a contrast fluid or pharmaceuticals into the cage 16 prior to retrieval of the cage 16. The pharmaceuticals may be, for example, a de-clotting agent that is used to de-clot areas of the body vessel 14. Alternatively, the aspirating source 66 may be used to grasp or suck out a clot and/or to facilitate entrapping a clot within the cage 16.

The device 10 may be comprised of any suitable material such as Nitinol, nickel-titanium alloy, shape-memory alloy, stainless steel, cobalt-chromium-nickel-molybdenum-iron alloy, or cobalt-chrome alloy. It is understood that the device 10 may be formed of any other suitable material that will result in the self-opening or self-expanding device 10, such as a shape memory material. Shape memory materials or alloys have the desirable property of becoming rigid, i.e. returning to a remembered state, when heated above a transition temperature. A shape memory alloy suitable for the present invention is Ni—Ti available under the more common name of Nitinol. When this material is heated above the transition temperature, the material undergoes a phase transformation from martensite to austenite, such that material returns to its remembered state. The transition temperature is dependent on the relative proportions of the alloying elements Ni and Ti and the optimal inclusion of alloy additives.

In one embodiment, the device is made from Nitinol with a transition temperature that is slightly below the normal body temperature of humans, which is about 98.6° F. Thus, when the device 10 is deployed in the body vessel 14 and exposed to normal body temperature, the alloy of the device 10 will transform to austenite, that is the remembered state, which for one embodiment of the present invention is the expanded state 32. To remove the device 10, the device is cooled to transform the material to martensite which is more ductile than austenite, making the device 10 more malleable. As such, the device 10 can be more easily collapsed and pulled into the lumen 48 of the sheath 46 for removal.

In another embodiment, the device 10 is made from Nitinol with a transition temperature that is above the normal body temperature of humans. Thus, when a device 10 is deployed in a body vessel 14 and exposed to the normal body temperature, the device 10 is in the martensitic state so that the device 10 is sufficiently ductile to bend or form into a desired shape, which for the present invention is the expanded state 32. To remove the device 10, the device 10 is heated to transform the alloy to austenite so that device 10 becomes rigid and returns to a remembered state, which for the device 10 is the collapsed state 42.

Referring to FIGS. 1a, 2a-2d and 4a-4b, a retrieval kit in accordance with at least one embodiment of the present invention is provided. As shown, the kit 70 includes the sheath 46 or micro-catheter defining a catheter lumen 48 and is preferably made of a soft, common material such as silicone or any other suitable material. Generally, the sheath 46 has a proximal end 72, a distal end 74, and a plastic adapter or hub 76 to receive the device 10 to be advanced therethrough. In one example, the inside diameter of the sheath 46 may range between 0.014 and 0.027 inches. The kit 70 may further include a guidewire 78 which provides a guide catheter 80 a path during insertion of the guide catheter 80 within the body vessel 14. The size of the guidewire 78 is based on the inside diameter of the guide catheter 80.

In one embodiment, the guide catheter 80 is a polytetrafluoroethylene (PTFE) guide catheter for percutaneously introducing the sheath 46 into the body vessel 14. Of course, any suitable material may be used without falling beyond the scope or spirit of the present invention. The guide catheter 80 may have a size of about 4-French to 8-French and allows the sheath 46 to be inserted therethrough to a desired location in the body vessel 14. The guide catheter 80 receives the sheath 46 and provides stability of the sheath 46 at a desired location in the body vessel 14. For example, the guide catheter 80 may stay stationery within a common visceral artery, e.g., a common hepatic artery, adding stability to the sheath 46 as the sheath 46 is advanced through the guide catheter 80 to a point where the foreign object 12 is located.

Referring to FIG. 5, a method for retrieving the foreign object within the body vessel is provided. The method includes deploying a retrieval device at 100 within the body vessel. The device includes a cage having a proximal end and distal end and a longitudinal axis extending between the proximal and distal ends. The cage is radially expanded at 102 about the longitudinal axis to form an opening at the distal end for receiving the foreign object. The cage is collapsed at 104 via a cable extending proximally from the proximal end of the cage for retrieval of the device at 106. The foreign object is retained therein such that the foreign object is substantially aligned with the longitudinal axis.

As a person skilled in the art will readily appreciate, the above description is meant as an illustration of the implementation of the principles of this invention. This description is not intended to limit the scope or application of this invention in that the invention is susceptible to modification, variation, and change, without departing from the spirit of this invention as defined in the following claims.

The invention claimed is:

1. A retrieval device for entrapping and retaining a foreign object located in a body vessel for its extraction therefrom, the device comprising:

a cage having a proximal end and a distal end and a longitudinal axis extending between the proximal and distal ends, the cage including:
  a plurality of longitudinal bars extending an entire length of the cage and between the proximal and distal ends, the longitudinal bars forming a cylindrical portion in an expanded state, the cylindrical portion defining a cylinder volume; and
  a plurality of struts connecting adjacent longitudinal bars, each strut having two ends adjoining the adjacent longitudinal bars and a pivotal joint disposed between the two ends, each strut extending proximally from the two ends to the pivotal joint to define a "V" shape in the expanded state, each strut being biased inwardly toward the longitudinal axis such that the pivotal joint is disposed within the cylinder volume in the expanded state to facilitate retaining the foreign object within the cage, the pivotal joints unfolding to move the longitudinal bars radially outward from the longitudinal axis, radially expanding the cage about the longitudinal axis to define the expanded state and forming an opening at the distal end for receiving the foreign object, and the pivotal joints folding to collapse the longitudinal bars along the longitudinal axis, collapsing the cage to define a collapsed state and to retain the foreign object therein such that the foreign object is substantially aligned with the longitudinal axis, the plurality of struts comprising a distal plurality of struts and a proximal plurality of struts, the distal plurality of struts forming a distal ring connected to each of the longitudinal bars and forming the distal end of the cage, the proximal plurality of struts forming a proximal ring connected to each of the longitudinal bars along the cylindrical portion and spaced apart from the distal ring, the longitudinal axis extending through a central point of the proximal ring and through a central point of the distal ring; and a cable extending proximally from the proximal end of the cage for retrieval of the device in the collapsed state, wherein the pivotal joints of the distal plurality of struts point toward the cable.

2. The retrieval device according to claim 1 wherein the cage is configured to be disposed within a sheath to restrain the cage in the collapsed state and to self-expand to the expanded state upon being advanced out of the sheath.

3. The retrieval device according to claim 1 wherein the cable has a lumen formed therethrough providing fluid communication between the cage and one of an aspirating source and an injection source.

4. The retrieval device according to claim 1 wherein the cage includes at least one of Nitinol, Nickel-Titanium alloy, shape memory alloy and stainless steel.

5. The retrieval device according to claim 1 wherein the cage in the expanded state has a maximum diameter less than a diameter of a lumen of the body vessel allowing the cage in the expanded state to be moved distally and proximally within the body vessel.

6. The retrieval device according to claim 1 wherein the struts in the expanded state are positioned at an angle to the longitudinal axis of less than about 45 degrees.

7. The retrieval device according to claim 1 wherein the struts are self-expanding and circumferentially aligned about at least one location along the longitudinal axis forming at least one ring that is connected to each of the longitudinal bars, providing radial force to expand the cage.

8. The retrieval device according to claim 7 wherein one of the at least one ring is formed at the distal end of the cage.

9. The retrieval device according to claim 1 wherein the cage further includes a connecting joint at the proximal end of the cage, each of the longitudinal bars being connected to the connecting joint which is connected to the cable.

10. The retrieval device according to claim 9 wherein the connecting joint has a diameter defined by the connection of the longitudinal bars with the connection joint, the diameter being less than a maximum diameter of the cage in the expanded state.

11. The retrieval device of claim 1, wherein the proximal ring is located at a proximal side of the cylindrical portion.

12. The retrieval device of claim 11, the plurality of struts further comprising a middle plurality of struts, the middle plurality of struts forming a middle ring connected to each of the longitudinal bars, the middle ring located about half way between the proximal ring and the distal ring.

13. A retrieval device for entrapping and retaining a foreign object located in a body vessel for its extraction therefrom, the device comprising:
a cage having a proximal end and a distal end, a longitudinal axis extending between the proximal and distal ends and a plurality of longitudinal bars extending an entire length of the cage and between the proximal end and the distal end, the longitudinal bars forming a cylindrical portion in an expanded state, the cylindrical portion defining a cylinder volume, the longitudinal axis extending through a center of the cylinder volume and being parallel to portions of each of the longitudinal bars that form the cylindrical portion, the cage being radially expandable about the longitudinal axis to define an expanded state and to form an opening at the distal end for receiving the foreign object, and being collapsible to define a collapsed state and to retain the foreign object therein such that the foreign object is substantially aligned with the longitudinal axis;
a plurality of struts each having a "V" shape with a pivotal joint disposed between two ends that connect adjacent longitudinal bars together, the pivotal joints unfolding to move the longitudinal bars radially outward from the longitudinal axis, each strut biased inwardly toward the longitudinal axis such that the pivotal joint is disposed within the cylinder volume in the expanded state to facilitate retaining the foreign object within the cage, the plurality of struts comprising a distal plurality of struts that form a distal ring connected to each of the longitudinal bars and forming the distal end of the cage; and
a cable extending proximally from the proximal end of the cage for retrieval of the device in the collapsed state, wherein the pivotal joints of the distal plurality of struts point toward the cable.

14. The retrieval device according to claim 13 wherein the cage is configured to be disposed within a sheath to restrain the cage in the collapsed state and to self-expand to the expanded state upon being advanced out of the sheath.

15. The retrieval device according to claim 13 wherein the cable has a lumen formed therethrough providing fluid communication between the cage and one of an aspirating source and an injection source.

16. The retrieval device according to claim 13 wherein the cage in the expanded state has a maximum diameter less than a diameter of a lumen of the body vessel allowing the cage in the expanded state to be moved distally and proximally within the body vessel.

17. A retrieval kit for entrapping and retaining a foreign object located in a body vessel for its extraction therefrom, the kit comprising:
a sheath for positioning in the body vessel; and
a retrieval device including:
a cage having a proximal end and a distal end, a longitudinal axis extending between the proximal and distal ends and a plurality of longitudinal bars extending an entire length of the cage and between the proximal and distal ends, the longitudinal bars forming a cylindrical portion in an expanded state, the cylindrical portion defining a cylinder volume, the longitudinal axis extending through a center of the cylinder volume and being parallel to portions of each of the longitudinal bars that form the cylindrical portion, the cage being radially expandable about the longitudinal axis to define an expanded state and to form an opening at the distal end for receiving the foreign object, and being collapsible to define a collapsed state and to retain the foreign object therein such that the foreign object is substantially aligned with the longitudinal axis, the cage configured to be disposed within the sheath in the collapsed state and to be advanced out of the sheath for expanding into the expanded state; and
a plurality of struts each having a "V" shape with a pivotal joint disposed between two ends that connect adjacent longitudinal bars together, the pivotal joints unfolding to move the longitudinal bars radially outward from the longitudinal axis, each strut biased inwardly toward the longitudinal axis such that the pivotal joint is disposed within the cylinder volume in the expanded state to facilitate retaining the foreign object within the cage, the plurality of struts comprising a distal plurality of struts that form a distal ring connected to each of the longitudinal bars and forming the distal end of the cage; and
a cable extending proximally from the proximal end of the cage for recovering the cage into the sheath to retrieve the device in the collapsed state, wherein the pivotal joints of the distal plurality of struts point toward the cable.

18. The kit according to claim 17 further comprising a guide catheter for percutaneous insertion into the body vessel and through which the sheath is inserted to position the sheath within the body vessel.

19. The kit according to claim 18 further comprising a guidewire for guiding the guide catheter in the body vessel.

20. The kit according to claim 17 wherein the cage includes:

a plurality of struts each having a pivotal joint and connecting the longitudinal bars together, the pivotal joints folding to collapse the longitudinal bars along the longitudinal axis defining the collapsed state of the cage and unfolding to move the longitudinal bars radially outward from the longitudinal axis defining the expanded state of the cage;

a connecting joint at the proximal end of the cage, each of the longitudinal bars being connected to the connecting joint which is connected to the cable; and wherein the plurality of longitudinal bars extending an entire length of the cage and between the proximal and distal ends of the cage;

wherein the struts are self-expanding and circumferentially aligned about at least one location along the longitudinal axis forming at least one ring that is connected to each of the longitudinal bars, providing radial force to expand the cage.

* * * * *